US008129174B2

(12) United States Patent
Alderborn et al.

(10) Patent No.: US 8,129,174 B2
(45) Date of Patent: Mar. 6, 2012

(54) SEPARATING METHOD AND AN APPARATUS PERFORMING SUCH A METHOD

(75) Inventors: Anders Alderborn, Uppsala (SE); David Peterson, Solna (SE); Bjorn Ingemarsson, Taby (SE); Anna-Lotta Schiller, Uppsala (SE)

(73) Assignee: Qiagen Instruments AG, Hombrechtikon (CH)

( * ) Notice: Subject to any disclaimer, the term of this patent is extended or adjusted under 35 U.S.C. 154(b) by 832 days.

(21) Appl. No.: 10/502,849

(22) PCT Filed: Feb. 12, 2003

(86) PCT No.: PCT/SE03/00231
§ 371 (c)(1),
(2), (4) Date: Jul. 29, 2004

(87) PCT Pub. No.: WO03/068962
PCT Pub. Date: Aug. 21, 2003

(65) Prior Publication Data
US 2005/0019775 A1 Jan. 27, 2005

(30) Foreign Application Priority Data

Feb. 12, 2002 (SE) ........................................ 0200415
Feb. 18, 2002 (SE) ........................................ 0200466

(51) Int. Cl.
*C12M 1/34* (2006.01)
*C12M 3/00* (2006.01)
*C12M 1/00* (2006.01)
*G01N 15/06* (2006.01)
*G01N 33/00* (2006.01)

(52) U.S. Cl. ............... 435/287.1; 435/283.1; 435/287.2; 422/68.1

(58) Field of Classification Search ............. 435/6, 91.1, 435/283.1, 287.1, 287.2; 422/50, 68.1; 530/300, 530/350; 424/130.1, 178.1
See application file for complete search history.

(56) References Cited

U.S. PATENT DOCUMENTS

| 4,424,279 | A | * | 1/1984 | Bohn et al. ..................... 436/534 |
| 4,637,229 | A | * | 1/1987 | Taylor, Jr. ....................... 66/146 |
| 5,034,135 | A | * | 7/1991 | Fischel .......................... 210/651 |
| 6,372,447 | B1 | * | 4/2002 | Raz ................................ 435/30 |

FOREIGN PATENT DOCUMENTS

| JP | 58-223759 | 12/1983 |
| WO | WO 9617084 | 6/1996 |
| WO | WO 0124937 | 4/2001 |

OTHER PUBLICATIONS

Romanin et al., Use of a 96 well format for wizard™ miniprep DNA isolation. Promega Notes Magazine, 49, p. 28, 1994.*

* cited by examiner

*Primary Examiner* — Frank W Lu
(74) *Attorney, Agent, or Firm* — Young & Thompson

(57) ABSTRACT

A method for separating carriers from a solution, the carriers being adapted to have biomolecules, such as DNA, RNA, proteins, polypeptides or carbohydrates attached thereto. The method includes the steps of introducing a tubular member (13) into a receptacle which holds a solution containing the carriers immersing an end portion of the tubular member in the solution attracting and holding the carriers to the end portion and removing the tubular member together with the held carriers from the solution. The attracting and holding step includes the step of providing an under-pressure within the tubular member so as to attract and hold the carriers to a filter (25) being disposed in the end portion of the tubular member. The invention also relates to an apparatus (10) performing such a method.

10 Claims, 3 Drawing Sheets

SEPARATING METHOD AND AN APPARATUS PERFORMING SUCH A METHOD

FIELD OF THE INVENTION

The present invention generally relates to a method for separating carriers from a solution; said carriers being adapted to have biomolecules attached thereto, and more particularly to a method using such a separation for the preparation of single stranded samples of genetic material. The present invention also relates to an apparatus for performing such methods. Finally, the present invention also relates to a disposable unit adapted to be attached to such an apparatus.

BACKGROUND OF THE INVENTION

Methods for analysing genetic material often require amplification of the nucleic acid sample as an initial step. This sometimes require the step of separating the two strands of a double-stranded DNA sample (dsDNA). In doing so, a related art method known as the Polymerase Chain Reaction (PCR) is employed. According to one variant of this method the dsDNA sample is amplified by the supply of a primer pair of which one is biotinylated, to a receptacle, which holds the solution containing the dsDNA sample. Streptavidin coated beads are then added to the solution, and by also adding a binding buffer the amplified dsDNA will be immobilised on the beads.

These beads may be made of sepharose, and one related art method for preparing single stranded DNA (ssDNA) is as follows: First, the receptacle holding the immobilised dsDNA is put on a vacuum station. The bottom of the receptacle is provided with a filter, which pore diameter is less than the size of the sepharose beads. Thus, when an under-pressure is applied on the underside of the filter the beads in the solution will be left on the filter, while the solution is drained away through the filter to, e.g. a liquid collector. In a next step, sodium hydroxide is supplied to the receptacle, which will separate the strands of the dsDNA into ssDNA, whereupon the sodium hydroxide is drained away. Thus, the ssDNA strands which are not bound to the beads are also drained away, while the bound ssDNA strands remain caught on the filter. In yet a further step, remaining sodium hydroxide is neutralised by means of an addition of washing buffer one or several times, and in a final step, in which the under-pressure is removed, a solution for re-suspending the caught beads in the solution is added. These beads having attached ssDNA strands are now ready to be transferred from this receptacle to an other receptacle for further preparation, or for analysis of the ssDNA.

However, it is difficult to fully re-suspend all beads in the solution since the beads are caught in the filter, and easily stick there despite the re-suspension attempts. Thus, trying to catch all beads by means of pipetting is difficult. Moreover, the situation is made worse when the heights of the liquid columns of the wells are low which yet render difficulties to the pipetting. Furthermore, the receptacle is commonly in the form of a multi-well receptacle, such as a Micro Titre Plate (MTP), having e.g. 96, 384, 1536 or 6144 separate wells, whereby a repetitive pipetting is disadvantageous from a strain injury point of view.

An other related art method disclosed in GB 99 233 249 uses magnetic beads instead of sepharose beads. According to this method a magnet is introduced into the receptacle, e.g. a well of a MTP, whereby the streptavidin coated magnetic beads are attracted to and hold by the magnet. Thus, the magnetic beads as well as the bound dsDNA may be removed from this receptacle and transferred to an other receptacle, in which e.g. a strand separating solution, such as sodium hydroxide is contained. Accordingly, the dsDNA will be separated into ssDNA, whereby the first strands are suspended in the solution, and optionally drained away, while the second strands remain bound to the beads. These latter strands may now be transferred to an other receptacle for further preparation, or for analysis.

However, magnetic beads are more expensive than sepharose beads, and the use of sepharose beads also results in better quality in a sequencing-by-synthesis method.

Furthermore, another related art method disclosed in U.S. Pat. No. 6,156,550 is related to transferring beads from one solution to another solution. This method describes how sepharose beads can be attached to a surface of a polymer. The drawback with beads bound to a support is that beads bound to a surface do not behave biochemically or physically similar to beads in a solution, thus further analysis of the ssDNA will be difficult.

In an other related art method disclosed in JP 58223759 beads are moved between two test tubes. A nozzle 16 is immersed in a first test tube 17 where it attracts a bead B by means of a vacuum. Then, the nozzle 16 is moved to a second test tube 18 where a back pressure is applied so as to release the bead B in the second test tube. During the whole movement the vacuum prevails within the nozzle. However, the nozzle is only capable of moving large beads, which are attracted to and stuck on the tip of the nozzle. In case of small beads, such beads would be drained away together with the liquid contained in the test tubes.

OBJECT OF THE INVENTION

An object of the present invention is to provide an improved method for separating carriers such as sepharose beads from solutions, said beads functioning as carriers for biomolecules.

SUMMARY OF THE INVENTION

This object is achieved according to the present invention by means of a method for separating carriers from a solution, said carriers being adapted to have biomolecules, such as DNA, RNA, proteins, polypeptides or carbohydrates attached thereto, wherein the method comprises the steps of introducing a tubular member into a receptacle which holds a solution containing said carriers; immersing an end portion of the tubular member in the solution; attracting and holding said carriers to said end portion; removing said tubular member together with the held carriers from the solution. The method is characterised in that said attracting and holding step comprises the step of providing an under-pressure within the tubular member so as to attract and hold the carriers to a filter being disposed in the end portion of the tubular member.

This object is also achieved by means of an apparatus for moving carriers between different receptacles, said carriers being adapted to have biomolecules, such as DNA, RNA, proteins, polypeptides or carbohydrates attached thereto, wherein the apparatus comprises at least one tubular member to be introduced into a receptacle, which contains a solution containing said carriers, said tubular member having an end portion to be immersed in the solution; and means for attracting and holding said carriers to said end portion. The apparatus is characterised in that said means comprises a filter being disposed in the end portion.

This object is also achieved by a method for preparing single stranded DNA (ssDNA) from double stranded DNA (dsDNA) comprising the steps of immobilising one of two strands of said dsDNA on carriers in a first receptacle holding a first solution, wherein the solution contains said carriers and said dsDNA; attracting and holding said carriers to a tubular member being immersed in the first solution; moving said tubular member together with the held carriers from the first receptacle to a second receptacle; separating the dsDNA into ssDNA in the second receptacle; removing the tubular member from the second receptacle, thus removing carriers with immobilised ssDNA from the second receptacle. The method is characterised in that said attracting and holding step comprises the step of providing an under-pressure within the tubular member so as to attract and hold the carriers to a filter being disposed in the tubular member.

This object is also achieved by a disposable unit adapted to be attached to the tubular member of an apparatus according to the preamble of claim 9, wherein said disposable unit is provided with a filter for holding said carriers.

By such a method and apparatus, carriers such as streptavidin coated sepharose beads may be transferred between different receptacles holding different solutions. Hereby, the whole procedure of preparing e.g. ssDNA or other manual sample preparation is simplified as well as less labour-intensive in comparison with the related art sepharose method, but also less expensive since the use of magnetic beads is avoided. Of course it is still possible to use the inventive methods and apparatus together with magnetic beads functioning as carriers for biomolecules.

Suitably, said methods comprise the step of releasing said carriers from the filter by removing the under-pressure or creating an over-pressure within the tubular member. Hereby, release of the carriers from the filter is enhanced.

Advantageously, each of the aforementioned steps is performed simultaneously at a plurality of locations. Hereby, the methods are adapted for use with a multi-well receptacles, such as Micro Titre Plates (MTR) with 96, 384, 1536 or 6144 wells.

Preferably, the method is used for purifying proteins, and more preferably for purifying tagged proteins, and most preferably for purifying His-tagged proteins. Hereby is achieved that a multi-well format purification could be applied for e.g. screening of recombinant bacteria for protein production.

Suitably, said apparatus comprises a housing having a sealed inner space which is connectable to a vacuum supply for creating an under-pressure inside the inner space, wherein the tubular member is in fluid communication with said inner space, and more suitably the tubular member projects into the inner space. Due to the projections, the solution will not flow back if the under-pressure is removed from the inner space, which prevent mixing of different solutions.

Preferably, the apparatus comprises a plurality of tubular members having a mutual arrangement corresponding to the arrangement of a multi-well receptacle. Hereby, the apparatus may be used with Micro Titre Plates (MTP).

Advantageously, all the tubular members are integrated in a separate support unit, which is detachable from the housing. Hereby, a disposable unit is provided. Furthermore, cleaning of tubes and filters is simplified.

Suitably, the apparatus comprises means or creating an over-pressure within the inner space. Hereby, the release of carriers which are trapped in the filter is facilitated.

Preferably, the apparatus comprises means for controlling the under-pressure and/or the over-pressure. Hereby, adaptation to different appliances is achieved.

Advantageously, the methods and/or the apparatus are used in an automatic robot system. Hereby, performance is improved since little human intervention is required. Accordingly, a robotic arm may carry the apparatus so as to, in an automated and non-human controlled way, transfer carriers between solutions and/or wells. In this respect, the releasing step may also be performed by shaking, vibrating or scraping so as to release the carriers from the filter after the under-pressure has been removed.

BRIEF DESCRIPTION OF THE DRAWINGS

A preferred embodiment of the present invention will now be described with reference to the accompanying drawings, on which:

FIG. 1b shows an exploded view of the apparatus in FIG. 1a;

FIG. 2c shows a view along section B-B of FIG. 2a;

FIG. 2d shows a view along section C-C of FIG. 2a;

FIG. 4a shows CBB stain and FIG. 4b shows Silver stain.

DETAILED DESCRIPTION

Figure 1A:
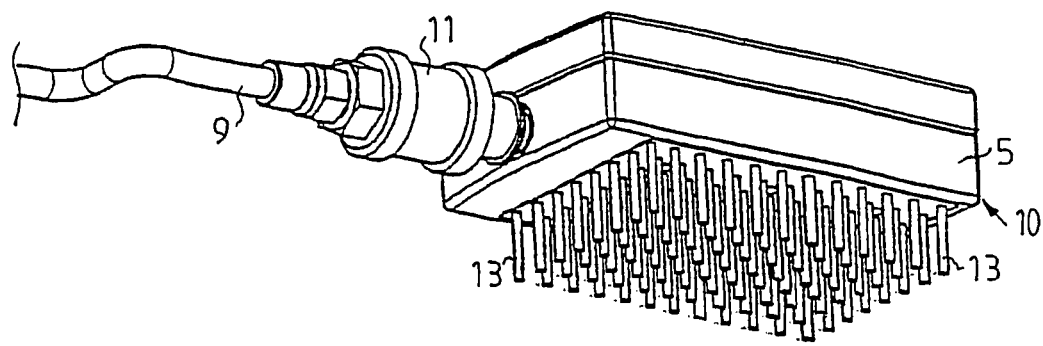
FIG. 1a shows a perspective view of an apparatus according to a preferred embodiment of the invention.
Figure 1B:
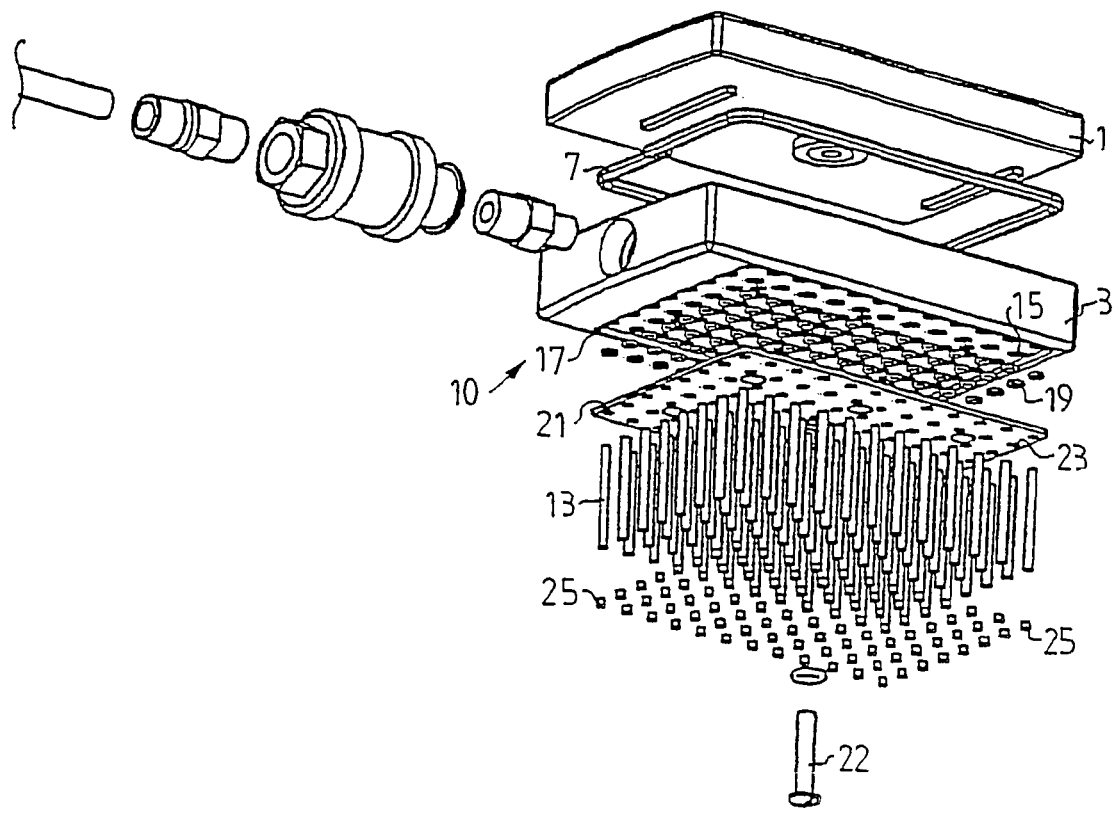

FIG. 1a-b show perspective views of an apparatus 10 in accordance with a preferred embodiment of the invention. The apparatus comprises a top cover 1 and a bottom cover 3 which together form a housing 5. A seal 7 is arranged between the top and bottom covers. A conduit 9 is in one end connected to the housing via a coupling 11, and in an other end connectable to, e.g. a not shown vacuum supply, a liquid separating device and/or a pressure supply. A plurality of tubular elongated members in the form of tubes 13 are each connected to openings 15 arranged on an underside 17 of the bottom cover 3. Sealing rings 19 are provided in each opening for sealing against the tubes 13. The tubes are arranged in parallel rows and columns corresponding to the arrangement of the wells of a multi-well receptacle, such as a Micro Titre Plate (MTP). A support plate 21 is by means of a screw 22 attached to the underside of the bottom cover, wherein the support plate is provided with a plurality of holes 23 adapted for the tubes and aligned with the openings in the bottom cover. A filter 25 is disposed in a cross-section in an end portion of each tube 13.

Figure 2A:
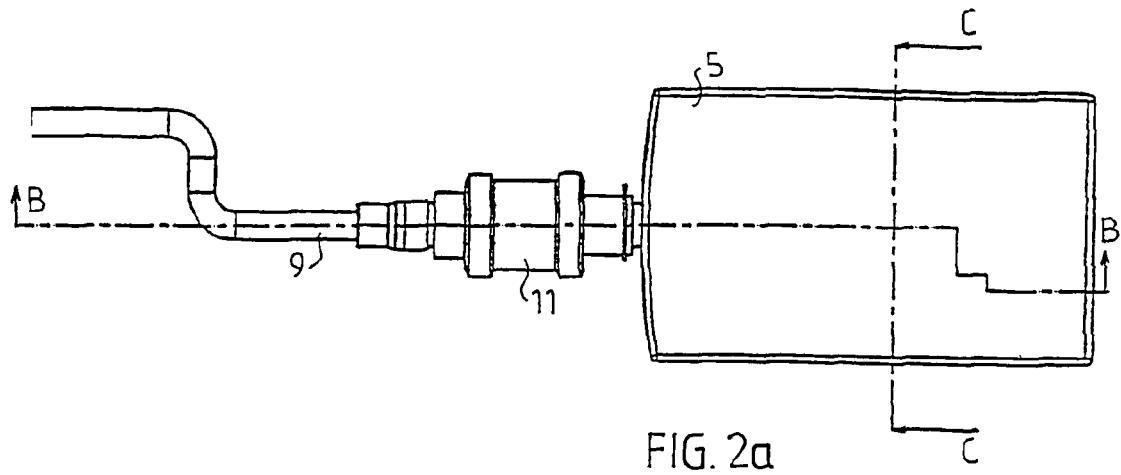
FIG. 2a shows a top view of the apparatus.
Figure 2B:
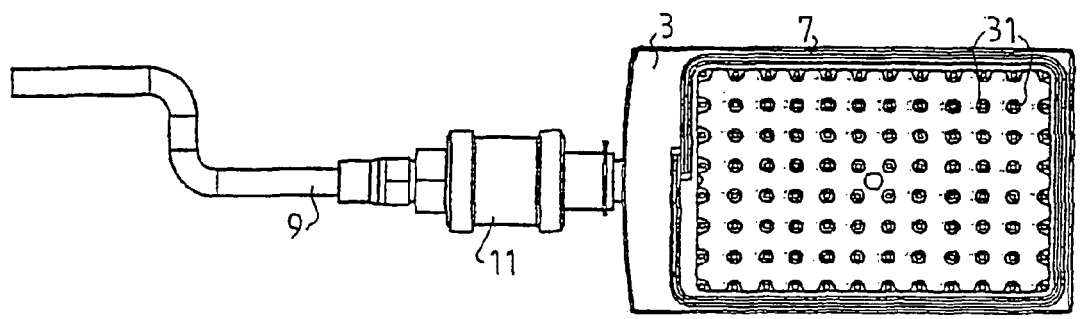
FIG. 2b shows a top view of the apparatus with a top cover being removed.
Figure 2C:
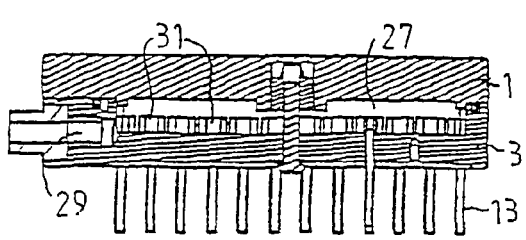
Figure 2D:
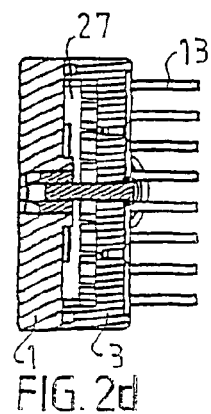

As can be seen from FIG. 2c an inner space 27 is created between the top 1 and bottom 3 covers when the top and bottom covers are assembled. This inner space is in fluid communication with the conduit 9 via a recess 29 arranged in a wall portion of the housing, and accordingly also in fluid communication with e.g. the vacuum supply mentioned earlier. The openings 15 of the bottom cover extend into the inner space, whereby each tube is in fluid communication with the inner space (this is shown in FIG. 2c for one or the tubes). As can be seen from FIGS. 2b-c, each tube also projects a short distance into the inner space, thus forming chimney-like protrusions 31.

Operation

The operation of the apparatus will be described solely by means of an example explaining the preparation of single stranded DNA samples typically comprising 50-2000 nucleotides. The skilled person will however realise that the apparatus is not restricted to this appliance only, but can be used in a number of appliances where carriers of biomolecules need to be separated from a solution or moved between different receptacles. As an example, even though streptavidin-biotin have been employed as binding molecule pair, in the above mentioned example, other binding molecules are also conceivable.

In the example, a multi-well receptacle, such as a MTP is provided (not shown), where each well holds a solution containing amplified double-stranded DNA samples, which have been immobilised on beads, such as streptavidin coated sepharose beads. The apparatus 10 is positioned above the MTP and subsequently lowered, whereby the tubes 13 of the apparatus are inserted into the wells of the MTP and then immersed in the solution. The vacuum supply is actuated whereby an under-pressure is provided in the inner space 27 of the housing 5, and thus also in each tube on a first side of the filter 25. By choosing a suitable under-pressure the solution is drawn into the tubes and through the filters. The solution enters the inner space and is subsequently drained away through the conduit 9 to a liquid separating device. The carriers with the immobilised beads are also drawn towards the filter, but are caught on a second side, i.e. opposite the first side, of the filter, while the solution is drained away through the filter. The filter is preferably made of a sintered material, such as sintered polypropylene plastic even though other materials are conceivable, and when the beads are made of sepharose having a diameter of approximately 38 μm the filter pore diameter needs to be about 10 μm.

The apparatus 10 may now be raised, with maintained under-pressure, thus removing the tubes having carriers held to the filter. The apparatus is moved to an other receptacle holding yet a solution in which e.g. a strand separating solution, such as sodium hydroxide is contained. Accordingly, the dsDNA will be separated into ssDNA when the tubes are immersed in the solution, whereby the first strands are suspended in the solution, while the second strands remain bound to the beads. The apparatus is then moved to an other MTP, wherein each well holds yet a solution. The tubes are immersed into the solution of the wells, and the vacuum supply is inactivated whereby the carriers are released from the filter and are re-suspended in the solution. The chimney-like protrusions 31 serve as to prevent solution contained in the inner space from flowing back to a receptacle when the vacuum supply is inactivated. Such back flow would otherwise risk to contaminate the solution present in a subsequent receptacle.

To facilitate the suspension the filter may be scraped against the bottom of the wells. The apparatus may also be shook or vibrated to further enhance the release of carriers. Alternatively, a pressure supply may be actuated, whereby an over-pressure is provided in the inner space of the housing, and thus also on the first side of each filter. This reversion of the pressure will further enhance the release of carriers from the second side of the filter by a blowing action through the filter, but also by creating a turbulent motion in the solution, thus having a rinsing effect of the filter. When the carriers are suspended in the solution, the pressure supply is inactivated, and the apparatus is raised thus removing the tubes from the wells. Now, the ssDNA preparation is completed, and suitable analysis of the ssDNA contained in the solution may commence. Such analysis may be sequencing or sequencing-by-synthesis as described in U.S. Pat. No. 5,405,746 and WO 98/13523, respectively.

After use of the apparatus cleaning of the filters may be required. The tubes are simply immersed in e.g. water or ethanol so as to rinse the filters, even though the. apparatus may be disassembled to completely clean the apparatus. To further improve the cleaning effect, the vacuum supply and/or the pressure supply may be actuated. In this case an alternation between an under-pressure and an over-pressure may be performed, which would improve the cleaning effect.

It is of course conceivable to design the support plate with integrated tubes and filters so as to create a disposable unit, which is thrown away after use. Such an unit is easily exchanged if required.

It is also conceivable to displace the filters a short distance from the outermost end portion of each tube. Thus, the capacity of holding carriers may be increased in case of solutions haling a high carrier density, or if high liquid columns occur in each well.

It is also possible that the carriers can be removed from the filter in the tubular member by treating them with ultrasound, for example by placing them in an ultrasonic water bath. In this way, the tubular members and filters will be cleaned before next usage.

Figure 3:
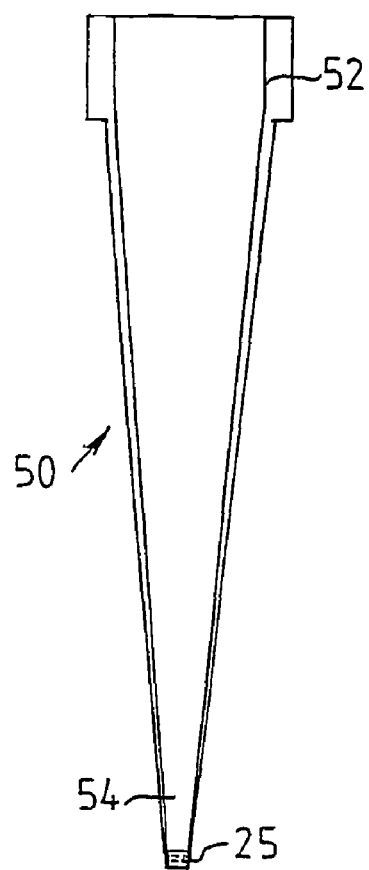
FIG. 3 shows a front view of a disposable unit according to another aspect of the present invention.

Moreover, it is also conceivable to provide the tubular members 13 with disposable tip units 50. Such an unit is shown in FIG. 3 and has a first end 52 to be connected to the tubular member 13 and a second end 54 to be immersed in the solution of a receptacle. The unit 50 has a tapered shape and is provided with a filter 25 for holding the carriers as described above, thus it is not necessary to provide the tubular members them selves with filters. These units are disposable and normally rejected after use.

Experiment

A study was also performed where the purpose was to investigate if it was possible to purify a His-tagged protein (HisKlenow) from a bacterial lysate with good selectivity and yield. In the description below, the use of the apparatus according to the present invention will only be described. in a general way and is only referred to as the inventive apparatus. The skilled man will however realise in conjunction with the DETAILED DESCRIPTION and OPERATION sections above how individual steps during purification of His-tagged proteins are to be performed with the aid of the inventive apparatus.

His-Klenow is the Klenow fragment of DNA polymerase with hexa-Histidine added N-terminally. The protein is over expressed in *E. coli* for production purposes. The introduced modification makes it possible to purify the protein by immobilized metal affinity chromatography (IMAC), using commercially available matrices. The procedure involves binding of the protein to immobilized $Ni^{2+}$-ions, washing out unbound substances and finally elution of the bound protein with buffer containing 0.2 M imidazol.

The study was performed by adoption of an related art method for chromatographic purification of His-Klenow to the inventive apparatus format. Since all critical parameters such as binding and elution properties was established, it was not necessary to study these further. The only variable was the amount of gel added to each well since this could be suspected to influence recovery.

| Materials | |
|---|---|
| HiTrap Chelating (1 ml) column | Amersham Biosciences |
| Lysate His-Klenow batch 1012 | |
| PCR-plates, 96-welll | Millipore |
| $NaH_2PO_4$ | Merck |
| NaCl | Merck |
| Imidazol | USB |
| The inventive apparatus | Pyrosequencing |
| Phast electrophoresis equipment | Amersham Biosciences |
| Phast 10–15% gels | Amersham Biosciences |

-continued

| Materials | |
|---|---|
| SDS buffer strips | Amersham Biosciences |
| Low Molecular Weight calibration kit | Amersham Biosciences |
| Commassie Brilliant Blue stain | Amersham Biosciences |
| Phast Silver stain kit | Amersham Biosciences |
| EDTA | Merck |
| Deionized water | |
| $NiCl_2 \times 6(H_2O)$ | Sigma |

Buffers

Binding and wash buffer: 10 mM $NaP_i$, 0.5 M NaCl, 10 mM imidazol, pH 7.4

Elution buffer: 10 mM $NaP_i$, 0.5 M NaCl, 0.2 M imidazol, pH 7.4

Preparation of the Gel

The gel was prepared according to instructions supplied by the manufacturer.
1. The column was washed with 50 mM EDTA, 2 ml
2. Wash with water, 5 ml
3. Charging with 0.1 M $NiCl_2$, 2 ml
4. Wash with water, 5 ml
5. Wash with binding buffer, 5 ml Subsequently the column was opened, the gel recovered and made to 50% slurry by addition of binding buffer.

SDS-PAGE and Staining

SDS-PAGE: method SDS 10-15
CBB staining: method SDS
Silver staining: method Ag
Methods refer to methods in the Phast electrophoresis equipment.

Figure 4A:
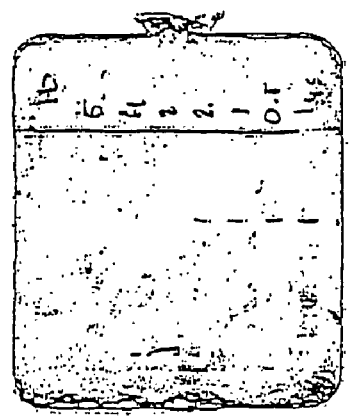
FIG. 4a-b show SDS-PAGE analysis of eluted proteins, where

Purification Using the Inventive Apparatus
1. 25 μl lysate was dispensed to 7 wells in a PCR-plate (column A)
2. 25 μl binding buffer was added to each well
3. 10, 5, 4, 3, 2, 1 and 0.5 μl gelslurry was added to well A-G, respectively
4. The plate was incubated for 5 min on a shaker
5. The inventive apparatus was used to aspirate the gel from the used wells
6. The gel was washed for 10-20 s by transfering the inventive apparatus to through containing binding buffer
7. Bound proteins were eluted by transfering the inventive apparatus to a fresh PCR-plate containing 50 μl elution buffer
8. A sample was withdrawn from each well for analysis. A sample of the starting material, i.e. lysate, was also taken.
9. SDS-PAGE was performed followed by staining with CBB or silver Results Analysis by SDS-PAGE shows that HisKlenow binds to the gel and can be recovered by treatment with elution buffer. See FIG. 4a-b. Both images have been manipulated to increase visibility of the scanned image. Numbers indicate the volume (μl) of gel (50% slurry) added to each well. "lys" indicates the starting material.

Discussion

In an initial experiment, a normal 96-well plate with much larger wells was used for binding and elution. It was obvious from this experiment that not much gel could aspirated from these much wider wells since remaining gel was clearly visible in the wells upon drying.

The subsequent experiment was performed in a PCR plate with concurrent variation of added gel volume. As can be seen in the FIG. 4a-b, the recovery increases with reduction of amount of added gel (see FIG. 4a, CBB stain). This is probably a reflection of that the subset of recovered gel is larger when low amounts of gel is used, leading to recovery of more protein. Thus it seems that the binding capacity of the gel is not a problem in this experiment.

Figure 4B:
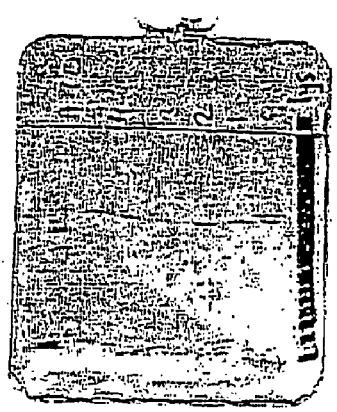

The purification efficiency is very good since no contaminants can be found in the eluted fractions as compared to the starting material (see FIG. 4b, Silver stained).

Conclusions

The inventive apparatus can be successfully used for isolation of proteins from complex mixtures, in this case a bacterial lysate. In this study, a His-tagged protein combined with a metal affinity gel was used as a model, but the principle should also work with other systems, e.g. an affinity gel, or protein-protein, or receptor ligand interactions.

The applied system was not optimized in any way which is a reason to suspect that improvements can be made with respect to both recovery and speed.

The invention claimed is:

1. An apparatus for moving carriers or beads between different receptacles, said carriers or beads containing biomolecules, the apparatus comprising:
   at least one tubular member having a first end portion adapted to be introduced into a receptacle, which holds a solution containing said carriers or beads, the first end portion being immersed in the solution;
   a filter disposed in a cross section of the first end portion such that the carriers or beads are caught by the surface of the filter exterior of the tubular member; and
   a housing having an inner space which is connectable to a vacuum supply for providing an under-pressure inside the inner space, wherein the at least one tubular member is in fluid communication with said inner space, and the at least one tubular member has a second portion that projects into the inner space.

2. The apparatus according to claim 1, further comprising means for creating at least one of an under-pressure and an over-pressure within the inner space.

3. The apparatus according to claim 2, further comprising means for controlling the over-pressure.

4. The apparatus according to claim 1, further comprising means for controlling the under-pressure.

5. The apparatus according to claim 1, wherein the filter is made of sintered material.

6. The apparatus according to claim 1, wherein the filter is made of sintered polypropylene plastic.

7. The apparatus according to claim 1, wherein said biomolecules comprise at least one of DNAs, RNAs, proteins, polypeptides or carbohydrates.

8. An apparatus for moving carriers or beads between different receptacles, said carriers or beads containing biomolecules, the apparatus comprising:
   a plurality of tubular members adapted to be introduced into a receptacle, which holds a solution containing said carriers or beads, each of said tubular members having an end portion to be immersed in the solution, wherein the receptacle is a multiple-well receptacle;
   a filter disposed in a cross section of the end portion such that the carriers or beads are caught by the surface of the filter exterior of each of the tubular members; and
   each of the plurality of tubular members inserting into each of the wells of the multiple-well receptacle and forming a mutual arrangement corresponding to the arrangement of the multi-well receptacle.

9. The apparatus according to claim 8, wherein the plurality of tubular member is integrated in a separate support unit, which is detachable from the housing.

10. The apparatus according to claim 8, wherein the multi-well receptacle is a micro titre plate (MTP).

* * * * *